United States Patent
Hühnlein et al.

(10) Patent No.: US 10,941,519 B2
(45) Date of Patent: Mar. 9, 2021

(54) PROCESS FOR REDUCTION OF ENERGY CONSUMPTION DURING THE PRETREATMENT OF BIOMASS

(71) Applicant: Clariant International Ltd., Muttenz (CH)

(72) Inventors: Björn Hühnlein, Straubing (DE); Thomas Hoppe, Landshut (DE); Ralf Hortsch, Munich (DE)

(73) Assignee: Clariant International Ltd., Muttenz (CH)

( * ) Notice: Subject to any disclaimer, the term of this patent is extended or adjusted under 35 U.S.C. 154(b) by 38 days.

(21) Appl. No.: 16/329,929

(22) PCT Filed: Aug. 22, 2017

(86) PCT No.: PCT/EP2017/071165
§ 371 (c)(1),
(2) Date: Mar. 1, 2019

(87) PCT Pub. No.: WO2018/041679
PCT Pub. Date: Mar. 8, 2018

(65) Prior Publication Data
US 2019/0185775 A1 Jun. 20, 2019

(30) Foreign Application Priority Data
Sep. 2, 2016 (EP) .................... 16187062

(51) Int. Cl.
*D21C 1/02* (2006.01)
*D21B 1/12* (2006.01)
*C10L 9/00* (2006.01)
*C10L 9/08* (2006.01)

(52) U.S. Cl.
CPC ............ *D21C 1/02* (2013.01); *C10L 9/00* (2013.01); *D21B 1/12* (2013.01); *C10L 9/086* (2013.01); *C12P 2201/00* (2013.01)

(58) Field of Classification Search
CPC . D21C 1/02–08; D21B 1/02–028; D21B 1/36
See application file for complete search history.

(56) References Cited

U.S. PATENT DOCUMENTS

2011/0250645 A1* 10/2011 Schiffino ............ C12P 7/00
435/72
2014/0110069 A1* 4/2014 Rawls ................ D21B 1/36
162/21

FOREIGN PATENT DOCUMENTS

| CN | 101765663 A | 6/2010 |
| CN | 101909713 A | 12/2010 |
| EP | 3045234 A1 | 7/2016 |

OTHER PUBLICATIONS

Chiaramonti et al., "Review of Pretreatment Processes for Lignocellulosic Ethanol Production, and Development of an Innovative Method", Biomass and Bioenergy 46 (2012) 25-35.
(Continued)

*Primary Examiner* — Anthony Calandra
(74) *Attorney, Agent, or Firm* — Verrill Dana, LLP (57) ABSTRACT

The present invention relates to a process for reduction of energy consumption during the pretreatment of biomass.

8 Claims, 2 Drawing Sheets

(56) References Cited

OTHER PUBLICATIONS

Maurya et al., "An Overview of Key Pretreatment Processes for Biological Conversion of Lignocellulosic Biomass to Bioethanol", 3 Biotech (2015) 5:597-609.
Maurya, D.P. et al., "An overview of key pretreatment processes for biological conversion of lignocellulosic biomass to bioethanol", 3 Biotech, (2015), vol. 5, pp. 597-609.

* cited by examiner

PROCESS FOR REDUCTION OF ENERGY CONSUMPTION DURING THE PRETREATMENT OF BIOMASS

The present invention relates to a process for reduction of energy consumption during the pretreatment of biomass.

Many organic biomasses have to undergo complex pretreatment processes in order to enable full use of its components. Conventional biomass pretreatment processes comprise the use of steam to break down the structure of the organic material. An efficient pretreatment method very commonly applied to e.g. lignocellulosic biomass is steam explosion. Within this type of pretreatment high amounts of steam are needed to pressurize the biomass up to a certain excess pressure before spontaneous expansion is initiated to disrupt the fibers. Consequently high energy costs occur rendering many pretreatment processes unprofitable for industrial scale applications.

Such a process is for example known from Chiaramonti D. et al., Review of pretreatment processes for lignocellulosic ethanol production, and development of an innovative method. Biomass and Bioenergy, 2012, 46:25-35.

The inventors of the present invention have now surprisingly found that steam consumption during such a pretreatment process can be minimized by optimization of feedstock processing during the process.

The inventors of the present invention therefore provide a process for reduction of energy consumption during the pretreatment of biomass characterized in that the feedstock processing parameter FPP is selected within the range of from 1.50 to 7.00

$$\frac{kg * \sqrt{\%}}{h * mm^2}.$$

The feedstock processing parameter is thereby determined as follows:

$$FPP = \frac{1}{\left(PRP\left(\frac{h}{kg\sqrt{\%}}\right) \times outletarea\ (mm^2)\right)} \times 100$$

Optimization of the feedstock processing is thereby carried out by adapting the outlet area of the reactor containing the pressurized biomass to the specific pretreatment resistance parameter of the biomass. The pretreatment resistance depends on lignin and xylose content as well as moisture content and the mass transfer rate of the respective biomass.

The "feedstock processing parameter" FPP may also be referred to as "biomass processing parameter" or "biomass transition parameter". All three terms are to be considered to be used synonymously. The pretreatment resistance parameter PRP is thereby determined as follows:

$$PRP = \frac{lignin\ (wt.\text{-}\%)}{\left(xylose\ (wt.\text{-}\%) \times \sqrt{moisture\ (wt.\text{-}\%)} \times \dot{m}\left(\frac{kg}{h}\right)\right)} \times 1000$$

The inventors of the present invention have therefore surprisingly found that pretreatment resistance of a certain feedstock depends on a specific ratio of lignin content to xylose content, moisture content and mass transfer rate. Mass transfer rate is usually predetermined by the respective pretreatment system as well as reactor and pipeline dimensions.

After determination of the PRP optimal and most energy efficient steam consumption will be ascertained by adapting the outlet area of an e.g. steam explosion pretreatment reactor to the respective PRP according to the inventive process. Within the present invention, steam explosion pretreatment is a preferred.

Within a preferred embodiment, the FPP is selected within the range of from 2.00 to 4.50

$$\left(\frac{kg * \sqrt{\%}}{h * mm^2}\right),$$

preferably from 2.50 to 4.00

$$\left(\frac{kg * \sqrt{\%}}{h * mm^2}\right),$$

particularly preferred from 2.2b to 3.90

$$\left(\frac{kg * \sqrt{\%}}{h * mm^2}\right),$$

wherein ranges from 2.25 to 3.80

$$\left(\frac{kg * \sqrt{\%}}{h * mm^2}\right)$$

and 2.25 to 3.75

$$\left(\frac{kg * \sqrt{\%}}{h * mm^2}\right)$$

are also preferred.

Selecting the FPP within the range of from 2.5 to 4.0

$$\left(\frac{kg * \sqrt{\%}}{h * mm^2}\right)$$

is thereby particularly preferred as a maximum of steam saving is achieved while general process conditions are most efficient with a low risk of plugging and economically favorable mass flow.

Within a further preferred embodiment the biomass is lignocellulosic biomass. Lignocellulosic biomass includes, but is not limited to plant material such as wheat straw, barley straw, rice straw, wood, wood chips, sawmill and paper mill discards, corn stover, sugarcane bagasse, and other agricultural residues, dedicated energy crops, municipal paper waste, and any other biomass material comprising cellulose, hemicellulose, xylose and lignin. The biomass material preferably has a dry matter (DM) content of from 30 to 95 wt.-%, further preferred of from 40 to 90 wt.-% and also preferred of from 50 to 85 wt.-%.

Within a preferred embodiment, the PRP is selected from the range of from 0.002 to 1.000

$$\left(\frac{h}{kg * \sqrt{\%}}\right).$$

preferably from 0.003 to 0.800

$$\frac{h}{kg * \sqrt{\%}},$$

further preferred from 0.004 to 0.550

$$\frac{h}{kg * \sqrt{\%}}$$

whereas ranges from 0.003 to 0.010

$$\frac{h}{kg * \sqrt{\%}}$$

and 0.004 to 0.009

$$\frac{h}{kg * \sqrt{\%}}$$

as well as 0.250 to 0.850

$$\frac{h}{kg * \sqrt{\%}}$$

and 0.300 to 0.750

$$\frac{h}{kg * \sqrt{\%}}$$

are also preferred. Ranges from 0.250 to 0.850

$$\frac{h}{kg * \sqrt{\%}}$$

and 0.300 to 0.750

$$\frac{h}{kg * \sqrt{\%}}$$

are preferred for small production sites and so called pilot scale plants with a mass transfer rate selected from the range of from 50 kg/h to 5 t/h. Ranges from 0.003 to 0.010

$$\frac{h}{kg * \sqrt{\%}}$$

and 0.004 to 0.009

$$\frac{h}{kg * \sqrt{\%}}$$

are preferred for big production sites with a mass transfer rate selected from the range of from more than 5 t/h to 100 t/h.

Within a further preferred embodiment the moisture content of the biomass is preferably from 5 to 60 wt.-%, preferably from 8 to 55 wt.-% and most preferred of from 10 to 50 wt.-%, whereas ranges from 10 to 25 wt.-% and 30 to 60 wt.-% are also preferred.

Within a further preferred embodiment the xylose content of the biomass is selected within the range of from 10.0 to 30.0 wt.-%, preferably from 17.0 to 27.0 wt.-%, particularly preferred from 20.0 to 25.0 wt.-% whereas ranges from 17.0 to 24.0 wt.-% and 18.0 to 23.0 wt.-% are also preferred.

Within a further preferred embodiment the steam pressure is selected within the range of from 8.0 to 15.0 bar, preferably from 8.5 to 12.5 and most preferred from 9.0 to 12.0 bar.

Within a further preferred embodiment the temperature during pretreatment is preferably selected within the range of from 150 to 200° C., preferably from 160 to 190° C. and most preferred of from 165 to 185° C.

Within a further preferred embodiment, the mass flow m is selected from the range of from 50 to 100,000 kg/h, preferably of from 100 to 50,000 kg/h, further preferred of from 250 to 35,000 kg/h and most preferred of from 400 to 25,000 kg/h. Ranges of from 50 kg/h to 5,000 kg/h and 250 kg/h to 1,000 kg/h are preferred for small production sites and so called pilot scale plants. Ranges from 5,000 kg/h to 50,000 kg/h and 10,000 to 25,000 kg/h are preferred for big, so-called industrial scale, production sites.

Within a further preferred embodiment the biomass pretreatment is carried out for a time selected from the range of from 1 minute to 20 minutes, preferably from 5 minutes to 15 minutes and most preferred of from 8 minutes to 10 minutes.

Figure 1:
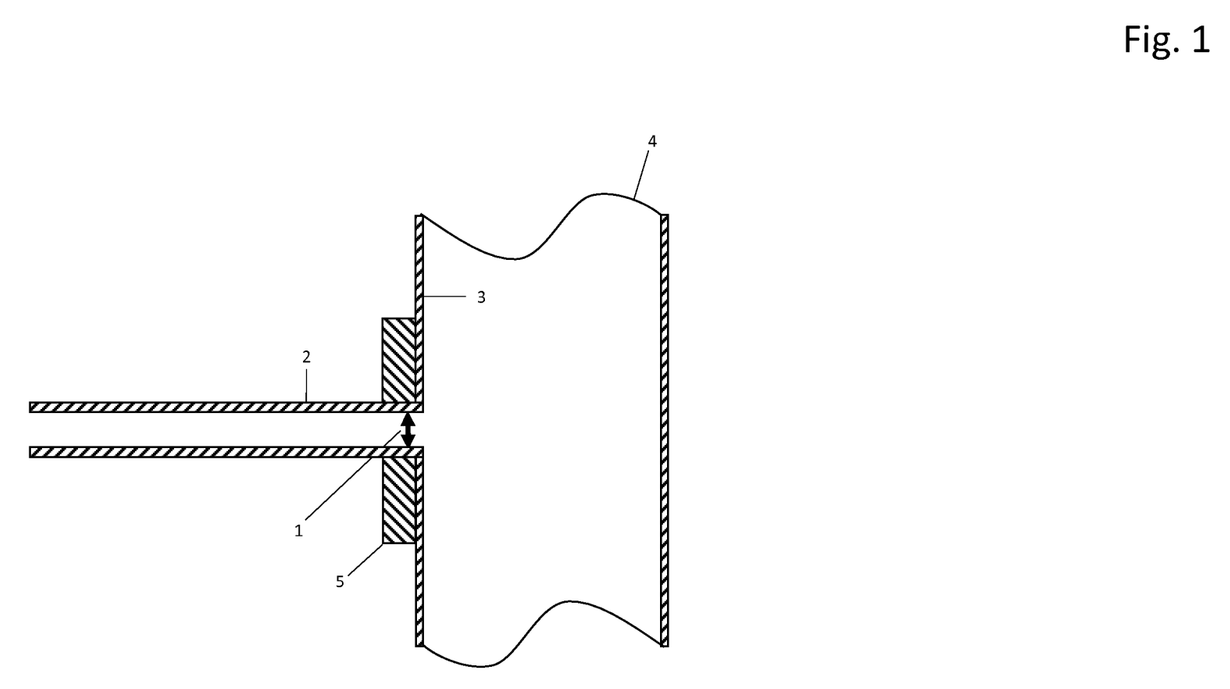
FIG. 1 shows a preferred location and embodiment of the outletarea OA of a steam explosion pretreatment reactor

Within the present application, the "outletarea" (OA) is defined as the area (measured in mm$^2$) as depicted within FIG. 1 (reference number (1)). The "outletarea" according to the present invention thereby constitutes the place where the pressurized biomass is leaving the reactor and is measured at the outer wall of the reactor (see also FIG. 1).

Within a preferred embodiment, the outletarea is selected from the range of from 10 to 17000 mm$^2$, preferably of from 30 to 10000 mm$^2$, further preferred of from 50 to 6700 mm$^2$, particularly preferred of from 55 to 5500 mm$^2$, also particularly preferred of from 60 to 4750 mm$^2$ and from 63 to 4500 mm$^2$. Whereas ranges of from 55 to 90 mm$^2$ and 60 to 75 mm$^2$ as well as from 3000 to 17000 mm$^2$ and from 4000 to 6300 mm$^2$ are also preferred. Ranges from 55 to 90 mm$^2$ and 60 to 75 mm$^2$ are preferred for small production sites and so called pilot scale plants with a mass transfer rate selected from the range of from 50 kg/h to 5 t/h. Ranges from 3000 to 17000 mm$^2$ and from 4000 to 6300 mm$^2$ are preferred for big production sites with a mass transfer rate selected from the range of from more than 5 t/h to 100 t/h.

Within a further preferred embodiment, the outlet area is a circle with a diameter selected from the range of from 2 to 150 mm, preferably from 4 to 100 mm and most preferred of from 8 to 75 mm, whereas ranges of from 2 to 15 mm and 4 to 20 mm as well as from 35 to 150 mm and from 40 to 100 mm and from 45 to 75 mm are also preferred. Ranges from 2 to 15 mm and 4 to 20 mm are preferred for small production sites and so called pilot scale plants with a mass transfer rate selected from the range of from 50 kg/h to 5 t/h. Ranges from 35 to 150 mm and from 40 to 100 mm as well as from 45 to 75 mm are preferred for big production sites with a mass transfer rate selected from the range of from more than 5 t/h to 100 t/h.

Figure 2:
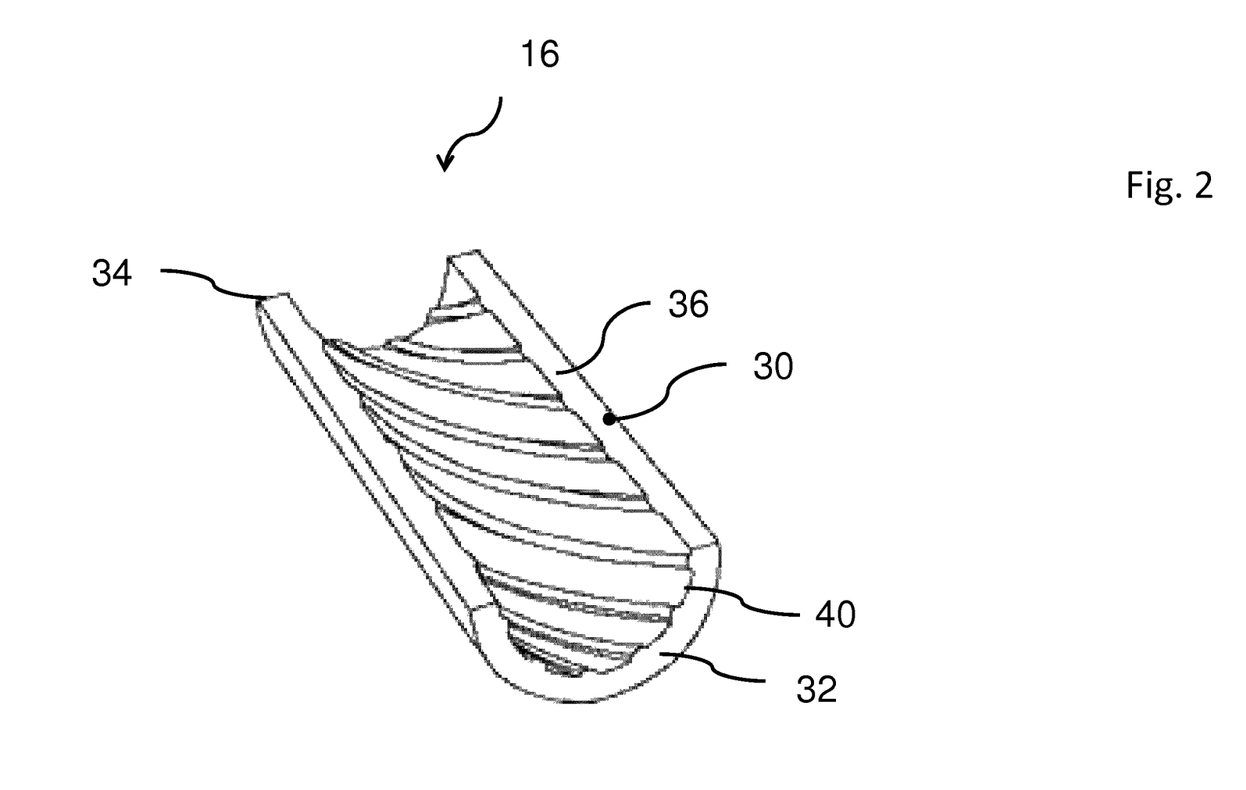

Within a particular preferred embodiment the outlet area is equipped with a nozzle as exemplarily depicted in FIG. 2.

The nozzle comprises a tubular body with a first open end and a second open end. The nozzle is adapted to be inserted into and coupled to an outlet opening of a steam explosion reactor, wherein the second open end is coupled to a conduit for conveying the pretreated biomass to at least one second device, preferably comprising a separator and the first open end is lining up with the inner wall of the reactor vessel or protruding into the reactor vessel. The inner surface of the tubular body of the nozzle comprises an engraved helical structure.

The engraved helical structure of the nozzle further reduces the steam consumption of the hydrothermal pre-treatment system considerably.

In a preferred embodiment the pitch of the engraved helical structure is in the range of from 1 to 300 mm, preferably from 10 to 150 mm, more preferably from 20 to 100 mm and most preferably from 30 to 60 mm. Particularly preferred are 30, 40, 50 and 60 mm.

The length of the nozzle is in the range of from 1 to 3500 mm, preferably from 10 to 1000 mm, and more preferably from 30 to 600 mm, further preferred from 60 to 500 mm. Most preferred are lengths of 50, 60, 80, 100, 200, 300, 400 and 500 mm. The length and the pitch of the engraved helical structure may suitable be chosen such that about 1 to 5 full convolutions and preferably 2 full convolutions are obtained.

The cross-sectional area of the inner surface of the nozzle is in the range of from 10 to 17,000 mm$^2$, preferably from 10 to 9000 mm$^2$, further preferred from 20 to 8000 mm$^2$, more preferably from 50 to 700 mm$^2$, also preferred of from 60 to 5000 mm$^2$. Further preferred ranges are from 10 to 150 mm$^2$, from 30 to 100 mm$^2$ and from 50 to 80 mm$^2$ as well as ranges of from 1000 mm$^2$ to 8000 mm$^2$, from 1500 to 7000 mm$^2$ and from 2000 to 6000 mm$^2$. The smaller the cross-sectional area of the inner surface of the nozzle, the smaller is the overall steam consumption.

The nozzle may have any suitable shape. However, preferably the cross-sectional shape of the inner surface of the nozzle is circular or ellipsoid, such that turbulences of the biomass material flow are reduced.

The depth of the engraved helical structure is in the range of from 0.1 to 15 mm, preferably of from 0.5 to 10 mm, and more preferably of from 1 to 5 mm, whereas of from 1.5 to 3 mm is also preferred.

The width of the engraved helical structure is in the range of from 0.1 to 3 mm, preferably of from 0.5 to 2 mm, and more preferably of from 1.0 to 1.5 mm.

The nozzle may generally be made from any material known to a person skilled in the art as suitable for the inventive purpose. The nozzles are preferably made from material of high abrasion resistance such as ceramic material, such as aluminium oxide, and more preferably from high purity aluminium oxide material, and most preferably from aluminium oxide having a purity of above 92% and more preferably having a purity of 99.7%, particularly preferred a purity of from 99.50 to 99.99%. An abrasion resistance of Vickers hardness of at least 1800 MPa is preferred. Particularly preferred is an abrasion resistance of at least 2000 MPa Vickers hardness wherein at least 2500 MPa are most preferred.

In a preferred embodiment, the nozzle is designed as depicted in FIG. 2. The nozzle 16 comprises a generally cylindrical tubular body 30 with a first open end 32 and a second open end 34. The tubular body 30 has generally circular cross-section. The inner wall surface 36 of the tubular body 30 is provided with an engraved helical structure. The depicted structures of FIG. 2 do not necessarily correspond to the actual dimensions of the nozzle 16. Only the lower half of a part of the nozzle 16 is depicted, such that the engraved helical structure at the inner wall surface 36 is visible. The helical structure consists of a plurality of grooves 40 having a depth of 1 mm and a width of 1.5 mm. The pitch of the grooves 40 amounts to 30 mm such that each groove 40 forms two convolutions along the full length of 60 mm of the nozzle 16.

The nozzle 16 depicted in FIG. 2 is preferably made from commercially available high purity aluminium oxide material ($Al_2O_3$ 99.7%). With a nozzle 16 made from this material, no abrasion was detected after 200 h of operation. Thus, the nozzle 16 not only reduces the required amount of steam in the hydrothermal pre-treatment of biomass, but the ceramic nozzle 16 also allows for smoother operation, since the pre-treatment process had not to be interrupted for maintenance.

Without limiting the scope of the present invention, the following embodiments of tables 1 to 4 are particularly preferred:

TABLE 1

| Moisture (%) | Outlet area OA (mm$^2$) | $PRP\left(\dfrac{h}{kg*\sqrt{\%}}\right)$ |
| --- | --- | --- |
| 25-45 | 65-80 | 0.250-0.375 |
| 25-45 | 4000-5500 | 0.0040-0.0065 |
| 10-20 | 30-90 | 0.40-0.70 |
| 10-20 | 4000-5000 | 0.007-0.009 |
| 10-18 | 60-75 | 0.50-0.60 |
| 10-18 | 4000-5500 | 0.007-0.009 |
| 15-30 | 60-70 | 0.40-0.70 |
| 15-30 | 3000-4500 | 0.008-0.010 |

Further preferred embodiments are defined in table 2

| Moisture (%) | Outlet area OA (mm$^2$) | $PRP\left(\dfrac{h}{kg*\sqrt{\%}}\right)$ | Temperature (° C.) |
| --- | --- | --- | --- |
| 25-45 | 65-80 | 0.250-0.375 | 160-190 |
| 25-45 | 4000-5500 | 0.0040-0.0065 | 160-190 |
| 10-20 | 30-90 | 0.40-0.70 | 160-190 |
| 10-20 | 4000-5000 | 0.007-0.009 | 160-190 |
| 10-18 | 60-75 | 0.50-0.60 | 160-190 |
| 10-18 | 4000-5500 | 0.007-0.009 | 160-190 |

-continued

| Moisture (%) | Outlet area OA (mm²) | PRP $\left(\dfrac{h}{kg*\sqrt{\%}}\right)$ | Temperature (° C.) |
|---|---|---|---|
| 15-30 | 60-70 | 0.40-0.70 | 160-190 |
| 15-30 | 3000-4500 | 0.008-0.010 | 160-190 |

Further preferred embodiments are defined in table 3

| Moisture (%) | Outlet area OA (mm²) | PRP $\left(\dfrac{h}{kg*\sqrt{\%}}\right)$ | Mass Flow $\dot{m}$ (kg/h) |
|---|---|---|---|
| 25-45 | 65-80 | 0.250-0.375 | 250-750 |
| 25-45 | 4000-5500 | 0.0040-0.0065 | 15,000-35,000 |
| 10-20 | 30-90 | 0.40-0.70 | 250-750 |
| 10-20 | 4000-5000 | 0.007-0.009 | 15,000-35,000 |
| 10-18 | 60-75 | 0.50-0.60 | 250-750 |
| 10-18 | 4000-5500 | 0.007-0.009 | 15,000-35,000 |
| 15-30 | 60-70 | 0.40-0.70 | 250-750 |
| 15-30 | 3000-4500 | 0.008-0.010 | 15,000-35,000 |

Further preferred embodiments are defined in table 4

| Moisture (%) | Outlet area OA (mm²) | PRP (h/kg√%) | Mass Flow $\dot{m}$ (kg/h) |
|---|---|---|---|
| 25-45 | 65-80 | 0.250-0.375 | 400 |
| 25-45 | 4000-5500 | 0.0040-0.0065 | 25,000 |
| 10-20 | 30-90 | 0.40-0.70 | 400 |
| 10-20 | 4000-5000 | 0.007-0.009 | 25,000 |
| 10-18 | 60-75 | 0.50-0.60 | 400 |
| 10-18 | 4000-5500 | 0.007-0.009 | 25,000 |
| 15-30 | 60-70 | 0.40-0.70 | 400 |
| 15-30 | 3000-4500 | 0.008-0.010 | 25,000 |

FIGURES AND EXAMPLES

The following examples and figures illustrate preferred embodiments of the invention but are not limiting the scope of the invention or claims.

FIG. 2 shows a preferred embodiment of a nozzle equipment Within FIG. 1 the reference number (1) is indicating the outlet area OA, reference number (2) is indicating a pipeline for conveying the pretreated biomass material to a second device, reference number (3) is indicating the outer wall of the pretreatment reactor (4) and reference number (5) is indicating a flange for fixation of the pipeline (2) to the reactor (4).

The composition of the biomass material was analyzed according to the NREL (National Renewable Energy Laboratory, USA) and ASE (Alliance for Sustainable Energy, LLC for the Department Of Energy) method: "Determination of Structural Carbohydrates and Lignin on Biomass", Version 08-03-2012.

The following components have been determined:
Dry matter content (DM)
Glucose (cellulose, glucan)
Xylose (xylan)
Ash
Lignin (insoluble in acid)
The results were adjusted by subtraction of the ash content for precise reference Exemplary calculation for example 1-0:
Dry matter content: 85.0%
Glucose (Cellulose, Glucan): 33.2%=>33.2%/((100−6.0%)/100)=35.3%
Xylose (Xylan) 21.3%=>21.3%/((100−6.0%)/100)=22.7%
Ash 6.0%
Lignin (insoluble in acid) 15.6%=>15.6%/((100−6.0%)/100)=16.6%
Moisture content was calculated by deduction of the DM measured: 15 wt.-%

Example 1-0 (Comparative) Wheat Straw (Moisture 15 wt.-%) FPP 0.7

$$\dfrac{kg*\sqrt{\%}}{h*mm^2}$$

Wheat straw bales were loosened up in a bale crusher (Tietjen) equipped with rotation scrappers operated at 3000 rpm yielding particles with particle sizes from 10 to 40 cm. This particle size ensures smooth transport of the material and operation of the subsequent milling step. The biomass material was pneumatically transported to a hammer mill (Tietjen VDK 4.1) operated at 3000 rpm with 30 mm sieves where the wheat straw was cut to pieces with an average particle sizes of from 1 to 5 cm.

The cut wheat straw was transported to the thermal pre-treatment reactor with a pin drum feeder (Metso; PDF 2545) followed by a transportation screw (Metso; FFS 211) and plug screw (Metso; ADI 180). The pin drum feeder adjusted a mass flow $\dot{m}$ of 400 kg (DM)/h. The wheat straw had a dry matter content of 85 wt.-%, a xylose content of 22.7 wt.-% and a lignin content of 16.6 wt.-% resulting in a PRP of 0.47

$$\left(\dfrac{h}{kg*\sqrt{\%}}\right).$$

In the pretreatment reactor vessel (Metso; RHA 740) the wheat straw was continuously pre-treated with steam at a temperature of 160° C. for 5 min without addition of any chemicals. The steam consumption was measured by Vortex Flowmeter Proline® from Endress & Hauser at 1.755 kg/h. After this hydrothermal pre-treatment, the pretreated wheat straw was transported to a cyclone (Schrader; DN1200) to separate the organic materials from the gases.

The pretreatment reactor vessel had an outlet with a cross-sectional area of about 283 mm² and the FPP (Feedstock Processing Parameter) was selected 0.7

$$\dfrac{kg*\sqrt{\%}}{h*mm^2}$$

The used steam amount per 1 kg DM was measured to 4.4 kg. Results are shown in table 5.

Example 1-A Wheat Straw (Moisture 15 wt.-%) FPP 3.3

Preparation of the Biomass was carried out as defined in example 1-0. The composition was identical to example 1-0 (PRP=0.47 $\left(\frac{h}{kg*\sqrt{\%}}\right)$.

The FPP (Feedstock Processing Parameter) was modified to 3.3 $\frac{kg*\sqrt{\%}}{h*mm^2}$ by adapting the outlet area to 65 mm². The steam consumption was measured to amount to 403 kg/h and corresponded to a specific steam consumption of 1.0 kg per 1 kg DM, which represented an effective reduction of steam consumption of 77% in comparison to example 1-0. Results are shown in table 5.

Example 1-B Wheat Straw (Moisture 15 wt.-%) FPP 2.3

Preparation of the Biomass was carried out as defined in example 1-0. The wheat straw had a dry matter content of 85 wt.-%, a xylose content of 21.3 wt.-% and a lignin content of 15.6 wt.-% resulting in a PRP of 0.47 $\left(\frac{h}{kg*\sqrt{\%}}\right)$.

The FPP (Feedstock Processing Parameter) was modified to 2.3 $\frac{kg*\sqrt{\%}}{h*mm^2}$ by adapting the outlet area to 90 mm². The steam consumption was measured to amount to 558 kg/h and corresponded to a specific steam consumption of 1.4 kg per 1 kg DM, which represented an effective reduction of steam consumption of 68.2% in comparison to example 1-0. Results are shown in table 5.

Example 1-C Wheat Straw (Moisture 15 wt.-%) FPP 7.0

Preparation of the Biomass was carried out as defined in example 1-0. The composition was identical to example 1-B (PRP=0.47 $\left(\frac{h}{kg*\sqrt{\%}}\right)$.

The FPP (Feedstock Processing Parameter) was modified to 7.0 $\frac{kg*\sqrt{\%}}{h*mm^2}$ by adapting the outlet area to 30 mm². The steam consumption was measured to amount to 186 kg/h and corresponded to a specific steam consumption of 0.5 kg per 1 kg DM. Results are shown in table 5.

Example 1-D Wheat Straw (Moisture 20 wt.-%) FPP 3.7

Preparation of the Biomass was carried out as defined in example 1-0. The wheat straw had a dry matter content of 80 wt.-%, a xylose content of 21.3 wt.-% and a lignin content of 15.6 wt.-% resulting in a PRP of 0.41 $\left(\frac{h}{kg*\sqrt{\%}}\right)$.

The FPP (Feedstock Processing Parameter) was modified to 3.7 $\frac{kg*\sqrt{\%}}{h*mm^2}$ by adapting the outlet area to 65 mm². The steam consumption was measured to amount to 403 kg/h and corresponded to a specific steam consumption of 1.0 kg per 1 kg DM, which represented an effective reduction of steam consumption of 77.0% in comparison to example 1-0. Results are shown in table 5.

Example 1-E Wheat Straw (Moisture 10 wt.-%) FPP 2.3

$$\frac{kg * \sqrt{\%}}{h * mm^2}$$

Preparation of the Biomass was carried out as defined in example 1-0. The wheat straw had a dry matter content of 90 wt.-%, a xylose content of 20.0 wt.-% and a lignin content of 17.0 wt.-% resulting in a PRP of 0.67

$$\left(\frac{h}{kg * \sqrt{\%}}\right).$$

The FPP (Feedstock Processing Parameter) was modified to 2.3

$$\frac{kg * \sqrt{\%}}{h * mm^2}$$

by adapting the outlet area to 65 mm². The steam consumption was measured to amount to 403 kg/h and corresponded to a specific steam consumption of 1.0 kg per 1 kg DM, which represented an effective reduction of steam consumption of 77.0% in comparison to example 1-0. Results are shown in table 5.

Example 2-0 (Comparative) Wheat Straw (Moisture 15 wt.-%) FPP 0.8

$$\frac{kg * \sqrt{\%}}{h * mm^2}$$

Wheat straw bales were loosened up in a bale crusher (Tietjen) equipped with rotation scrappers operated at 3000 rpm yielding particles with particle sizes from 10 to 40 cm. This particle size ensures smooth transport of the material and operation of the subsequent milling step. The biomass material was pneumatically transported to a hammer mill (Tietjen) operated at 3000 rpm with 30 mm sieves where the wheat straw was cut to pieces with an average particle sizes of from 1 to 5 cm.

The cut wheat straw was transported to the thermal pre-treatment reactor with a pin drum feeder (Metso) followed by a transportation screw (Metso) and plug screw (Metso). The pin drum feeder adjusted a mass flow ṁ of 25,000 kg (DM)/h. The composition was identical to example 1-B (PRP=0.008

$$\left(\frac{h}{kg * \sqrt{\%}}\right).$$

In the pretreatment reactor vessel (Metso) the wheat straw was continuously pre-treated with steam at a temperature of 160° C. for 5 min without addition of any chemicals. The steam consumption was measured by Vortex Flowmeter Proline® from Endress & Hauser at 1.755 kg/h. After this hydrothermal pre-treatment, the pretreated wheat straw was transported to a cyclone (Schrader) to separate the organic materials from the gases.

The FPP (Feedstock Processing Parameter) was modified to 0.8

$$\frac{kg * \sqrt{\%}}{h * mm^2}$$

by adapting the outlet area to 16,000 mm². The steam consumption was measured to amount to 99,200 kg/h and corresponded to a specific steam consumption of 4.0 kg per 1 kg DM. Results are shown in table 5.

Example 2-A Wheat Straw (Moisture 15 wt.-%) FPP 3.1

$$\frac{kg * \sqrt{\%}}{h * mm^2}$$

Preparation of the Biomass was carried out as defined in example 2-0. The composition was identical to example 2-0 (PRP=0.008

$$\left(\frac{h}{kg * \sqrt{\%}}\right).$$

The FPP (Feedstock Processing Parameter) was modified to 3.1

$$\frac{kg * \sqrt{\%}}{h * mm^2}$$

by adapting the outlet area to 4,200 mm². The steam consumption was measured to amount to 26,040 kg/h and corresponded to a specific steam consumption of 1.0 kg per 1 kg DM which represented an effective reduction of steam consumption of 73.8% in comparison to example 2-0. Results are shown in table 5.

Example 3-0 (Comparative) Corn Stover (Moisture 17 wt.-%) FPP 0.6

$$\frac{kg * \sqrt{\%}}{h * mm^2}$$

Preparation of the Biomass was carried out as defined in example 1-0. The corn stover had a dry matter content of 83 wt.-%, a xylose content of 19.7 wt.-% and a lignin content of 17.8 wt.-% resulting in a PRP of 0.547

$$\left(\frac{h}{kg * \sqrt{\%}}\right).$$

The FPP (Feedstock Processing Parameter) was modified to 0.6

$$\frac{kg * \sqrt{\%}}{h * mm^2}$$

by adapting the outlet area to 283 mm². The steam consumption was measured to amount to 1811 kg/h and corresponded to a specific steam consumption of 4.5 kg per 1 kg DM. Results are shown in table 5.

Example 3-A Corn Stover (Moisture 17 wt.-%) FPP 0.6

$$\frac{kg * \sqrt{\%}}{h * mm^2}$$

Preparation of the Biomass was carried out as defined in example 1-0. The corn stover was identical to example 3-0 (PRP of 0.547

$$\left(\frac{h}{kg * \sqrt{\%}}\right)).$$

The FPP (Feedstock Processing Parameter) was modified to 2.9

$$\frac{kg * \sqrt{\%}}{h * mm^2}$$

by adapting the outlet area to 63 mm². The steam consumption was measured to amount to 403 kg/h and corresponded to a specific steam consumption of 1.0 kg per 1 kg DM which represented an effective reduction of steam consumption of 77.7% in comparison to example 3-0. Results are shown in table 5.

Example 3-B Corn Stover (Moisture 30 wt.-%) FPP 0.6

$$\frac{kg * \sqrt{\%}}{h * mm^2}$$

Preparation of the Biomass was carried out as defined in example 1-0. The corn stover had a dry matter content of 70 wt.-%, a xylose content of 19.7 wt.-% and a lignin content of 17.8 wt.-% resulting in a PRP of 0.412

$$\left(\frac{h}{kg * \sqrt{\%}}\right).$$

The FPP (Feedstock Processing Parameter) was modified to 3.6

$$\frac{kg * \sqrt{\%}}{h * mm^2}$$

by adapting the outlet area to 67 mm². The steam consumption was measured to amount to 429 kg/h and corresponded to a specific steam consumption of 1.1 kg per 1 kg DM which represented an effective reduction of steam consumption of 76.3% in comparison to example 3-0. Results are shown in table 5.

Example 4-0 (Comparative) Corn Stover (Moisture 17 wt.-%) FPP 0.7

$$\frac{kg * \sqrt{\%}}{h * mm^2}$$

Preparation of the Biomass was carried out as defined in example 2-0. The corn stover was identical to example 3-0 resulting in a PRP of 0.009

$$\left(\frac{h}{kg * \sqrt{\%}}\right).$$

The FPP (Feedstock Processing Parameter) was modified to 0.7

$$\frac{kg * \sqrt{\%}}{h * mm^2}$$

by adapting the outlet area to 16,000 mm². The steam consumption was measured to amount to 102,400 kg/h and corresponded to a specific steam consumption of 4.1 kg per 1 kg DM. Results are shown in table 5.

Example 4-A Corn Stover (Moisture 17 wt.-%) FPP 3.0

$$\frac{kg * \sqrt{\%}}{h * mm^2}$$

Preparation of the Biomass was carried out as defined in example 4-0. The corn stover was identical to example 3-0 resulting in a PRP of 0.009

$$\left(\frac{h}{kg * \sqrt{\%}}\right).$$

The FPP (Feedstock Processing Parameter) was modified to 3.0

$$\frac{kg * \sqrt{\%}}{h * mm^2}$$

by adapting the outlet area to 3,800 mm². The steam consumption was measured to amount to 24,320 kg/h and corresponded to a specific steam consumption of 1.0 kg per 1 kg DM which represented an effective reduction of steam consumption of 76.3% in comparison to example 4-0. Results are shown in table 5.

Example 5-0 (Comparative) Barley Straw (Moisture 13 wt.-%) FPP 0.7

$$\frac{kg * \sqrt{\%}}{h * mm^2}$$

Preparation of the Biomass was carried out as defined in example 1-0. The barley straw had a dry matter content of 87 wt.-%, a xylose content of 18.8 wt.-% and a lignin content of 14.2 wt.-% resulting in a PRP of 0.521

$$\left(\frac{h}{kg * \sqrt{\%}}\right).$$

The FPP (Feedstock Processing Parameter) was modified to 0.7

$$\frac{kg * \sqrt{\%}}{h * mm^2}$$

by adapting the outlet area to 283 mm². The steam consumption was measured to amount to 1,641 kg/h and corresponded to a specific steam consumption of 4.1 kg per 1 kg DM. Results are shown in table 5.

Example 5-A Barley Straw (Moisture 13 wt.-%) FPP 2.9

$$\frac{kg * \sqrt{\%}}{h * mm^2}$$

Preparation of the Biomass was carried out as defined in example 5-0. The barley straw was identical to example 5-0 resulting in a PRP of 0.521

$$\left(\frac{h}{kg * \sqrt{\%}}\right).$$

The FPP (Feedstock Processing Parameter) was modified to 2.9

$$\frac{kg * \sqrt{\%}}{h * mm^2}$$

by adapting the outlet area to 66 mm². The steam consumption was measured to amount to 383 kg/h and corresponded to a specific steam consumption of 1.0 kg per 1 kg DM which represented an effective reduction of steam consumption of 76.7% in comparison to example 5-0. Results are shown in table 5.

Example 6-0 (Comparative) Barley Straw (Moisture 13 wt.-%) FPP 0.7

$$\frac{kg * \sqrt{\%}}{h * mm^2}$$

Preparation of the Biomass was carried out as defined in example 2-0. The barley straw was identical to example 5-0 resulting in a PRP of 0.008

$$\left(\frac{h}{kg * \sqrt{\%}}\right).$$

The FPP (Feedstock Processing Parameter) was modified to 0.7

$$\frac{kg * \sqrt{\%}}{h * mm^2}$$

by adapting the outlet area to 16,000 mm². The steam consumption was measured to amount to 92,800 kg/h and corresponded to a specific steam consumption of 3.7 kg per 1 kg DM. Results are shown in table 5.

Example 6-A Barley Straw (Moisture 13 wt.-%) FPP 2.7

$$\frac{kg * \sqrt{\%}}{h * mm^2}$$

Preparation of the Biomass was carried out as defined in example 6-0. The barley straw was identical to example 6-0 resulting in a PRP of 0.008

$$\left(\frac{h}{kg * \sqrt{\%}}\right).$$

The FPP (Feedstock Processing Parameter) was modified to 2.7

$$\frac{kg * \sqrt{\%}}{h * mm^2}$$

by adapting the outlet area to 4,500 mm². The steam consumption was measured to amount to 26,100 kg/h and corresponded to a specific steam consumption of 1.0 kg per 1 kg DM which represented an effective reduction of steam consumption of 71.9% in comparison to example 6-0. Results are shown in table 5.

Example 7-0 (Comparative) Bagasse (Moisture 40 wt.-%) FPP 1.0

$$\frac{kg * \sqrt{\%}}{h * mm^2}$$

Preparation of the Biomass was carried out as defined in example 1-0. The bagasse had a dry matter content of 60 wt.-%, a xylose content of 22.0 wt.-% and a lignin content of 19.2 wt.-% resulting in a PRP of 0.345

$$\left(\frac{h}{kg * \sqrt{\%}}\right).$$

The FPP (Feedstock Processing Parameter) was modified to 1.0

$$\frac{kg * \sqrt{\%}}{h * mm^2}$$

by adapting the outlet area to 283 mm². The steam consumption was measured to amount to 1,557 kg/h and corresponded to a specific steam consumption of 3.9 kg per 1 kg DM. Results are shown in table 5.

Example 7-A Bagasse (Moisture 40 wt.-%) FPP 3.9

$$\frac{kg * \sqrt{\%}}{h * mm^2}$$

Preparation of the Biomass was carried out as defined in example 7-0. The bagasse was identical to example 7-0 resulting in a PRP of 0.345

$$\left(\frac{h}{kg * \sqrt{\%}}\right).$$

The FPP (Feedstock Processing Parameter) was modified to 3.9

$$\frac{kg * \sqrt{\%}}{h * mm^2}$$

by adapting the outlet area to 74 mm². The steam consumption was measured to amount to 407 kg/h and corresponded to a specific steam consumption of 1.0 kg per 1 kg DM which represented an effective reduction of steam consumption of 73.9% in comparison to example 7-0. Results are shown in table 5.

Example 8-0 (Comparative) Bagasse (Moisture 40 wt.-%) FPP 1.1

$$\frac{kg * \sqrt{\%}}{h * mm^2}$$

Preparation of the Biomass was carried out as defined in example 2-0. The bagasse was identical to example 7-0 resulting in a PRP of 0.006

$$\left(\frac{h}{kg * \sqrt{\%}}\right).$$

The FPP (Feedstock Processing Parameter) was modified to 1.1

$$\frac{kg * \sqrt{\%}}{h * mm^2}$$

by adapting the outlet area to 16,000 mm². The steam consumption was measured to amount to 88,000 kg/h and corresponded to a specific steam consumption of 3.5 kg per 1 kg DM. Results are shown in table 5.

Example 8-A Bagasse (Moisture 40 wt.-%) FPP 3.8

$$\frac{kg * \sqrt{\%}}{h * mm^2}$$

Preparation of the Biomass was carried out as defined in example 8-0. The bagasse was identical to example 8-0 resulting in a PRP of 0.006

$$\left(\frac{h}{kg * \sqrt{\%}}\right).$$

The FPP (Feedstock Processing Parameter) was modified to 3.8

$$\frac{kg * \sqrt{\%}}{h * mm^2}$$

by adapting the outlet area to 4,750 mm². The steam consumption was measured to amount to 26,125 kg/h and corresponded to a specific steam consumption of 1.0 kg per 1 kg DM which represented an effective reduction of steam consumption of 70.3% in comparison to example 8-0. Results are shown in table 5.

TABLE 5

| Example | Xylose (Xylan) [wt. %] | Lignin [wt. %] | Moisture [wt. %] | Mass Flow ṁ [kg/h] | Outlet area OA [mm²] | PRP $\left[\dfrac{h}{kg*\sqrt{\%}}\right]$ | Steam Consumption [kg/(mm²*h)] | Steam Consumption [kg/h] | Steam Consumption [kg(steam)/kg(TS)] | Steam Saving [%] | FPP $\left[\dfrac{kg*\sqrt{\%}}{h*mm^2}\right]$ |
|---|---|---|---|---|---|---|---|---|---|---|---|
| 1-0 | 22.7 | 16.6 | 15 | 400 | 283 | 0.47 | 6.2 | 1,755 | 4.4 | | 0.7 |
| 1-A | 22.7 | 16.6 | 15 | 400 | 65 | 0.47 | 6.2 | 403 | 1.0 | 77.0 | 3.3 |
| 1-B | 21.3 | 15.6 | 15 | 400 | 90 | 0.47 | 6.2 | 558 | 1.4 | 68.2 | 2.3 |
| 1-C | 21.3 | 15.6 | 15 | 400 | 30 | 0.47 | 6.2 | 186 | 0.5 | 89.4 | 7.0 |
| 1-D | 21.3 | 15.6 | 20 | 400 | 65 | 0.41 | 6.2 | 403 | 1.0 | 77.0 | 3.7 |
| 1-E | 20.0 | 17.0 | 10 | 400 | 65 | 0.67 | 6.2 | 403 | 1.0 | 77.0 | 2.3 |
| 2-0 | 21.3 | 15.6 | 15 | 25,000 | 16,000 | 0.008 | 6.2 | 99,200 | 4.0 | | 0.8 |
| 2-A | 21.3 | 15.6 | 15 | 25,000 | 4,200 | 0.008 | 6.2 | 26,040 | 1.0 | 73.8 | 3.1 |
| 3-0 | 19.7 | 17.8 | 17 | 400 | 283 | 0.547 | 6.4 | 1,811 | 4.5 | | 0.6 |
| 3-A | 19.7 | 17.8 | 17 | 400 | 63 | 0.547 | 6.4 | 403 | 1.0 | 77.7 | 2.9 |
| 3-B | 19.7 | 17.8 | 30 | 400 | 67 | 0.412 | 6.4 | 429 | 1.1 | 76.3 | 3.6 |
| 4-0 | 19.7 | 17.8 | 17 | 25,000 | 16,000 | 0.009 | 6.4 | 102,400 | 4.1 | | 0.7 |
| 4-A | 19.7 | 17.8 | 17 | 25,000 | 3,800 | 0.009 | 6.4 | 24,320 | 1.0 | 76.3 | 3.0 |
| 5-0 | 18.8 | 14.2 | 13 | 400 | 283 | 0.521 | 5.8 | 1,641 | 4.1 | | 0.7 |
| 5-A | 18.8 | 14.2 | 13 | 400 | 66 | 0.521 | 5.8 | 383 | 1.0 | 76.7 | 2.9 |
| 6-0 | 18.8 | 14.2 | 13 | 25,000 | 16,000 | 0.008 | 5.8 | 92,800 | 3.7 | | 0.7 |
| 6-A | 18.8 | 14.2 | 13 | 25,000 | 4,500 | 0.008 | 5.8 | 26,100 | 1.0 | 71.9 | 2.7 |
| 7-0 | 22.0 | 19.2 | 40 | 400 | 283 | 0.345 | 5.5 | 1,557 | 3.9 | | 1.0 |
| 7-A | 22.0 | 19.2 | 40 | 400 | 74 | 0.345 | 5.5 | 407 | 1.0 | 73.9 | 3.9 |
| 8-0 | 22.0 | 19.2 | 40 | 25,000 | 16,000 | 0.006 | 5.5 | 88,000 | 3.5 | | 1.1 |
| 8-A | 22.0 | 19.2 | 40 | 25,000 | 4,750 | 0.006 | 5.5 | 26,125 | 1.0 | 70.3 | 3.8 |

The invention claimed is:

1. Process for reduction of energy consumption during steam pretreatment of a lignocellulosic biomass, the process comprising
   (a) determining for the lignocellulosic biomass feedstuff a pretreatment resistance parameter PRP, which is defined as $$PRP = \dfrac{lignin(\text{wt.-}\%)}{\left(xylose(\text{wt.-}\%) \times \sqrt{moisture(\text{wt.-}\%) \times \dot{m}\left(\dfrac{kg}{h}\right)}\right)} \times 1000,$$

wherein lignin, xylose, moisture, and ṁ (as dry matter) refer to features of the lignocellulosic biomass;
   (b) determining a range of reactor steam outlet cross-sectional area using a feedstock processing parameter, which is defined as $$FPP = \dfrac{1}{\left(PRP\left(\dfrac{h}{kg\sqrt{\%}}\right) \times outletarea(mm^2)\right)} \times 100,$$

wherein FPP is within the range of from 2.0 to 4.5

$$\dfrac{kg * \sqrt{\%}}{h * mm^2};$$

(c) adjusting the reactor steam outlet cross-sectional area of a reactor to a value within the range determined in (b); and
   (d) carrying out steam pretreatment of the lignocellulosic biomass, wherein steam consumption is reduced compared to using a reactor outlet cross-sectional area outside of said range.

2. Process according to claim 1, wherein the pretreatment resistance parameter PRP of the lignocellulosic biomass is within the range of from 0.002 to 1.000

$$\dfrac{h}{kg*\sqrt{\%}}.$$

3. Process according to claim 2, wherein the pretreatment resistance parameter PRP of the lignocellulosic biomass is within the range of from 0.003 to 0.80

$$\dfrac{h}{kg*\sqrt{\%}}.$$

4. Process according to claim 1, wherein the lignocellulosic biomass has a lignin wt % to glucose wt % ratio of from 0.35 to 0.60.

5. Process according to claim 1, wherein the moisture content of the lignocellulosic biomass is within the range of from 5 to 60 wt %.

6. Process according to claim 1, wherein the xylose content of the lignocellulosic biomass is within the range of from 10.0 to 30.0 wt %.

7. Process according to claim 1, wherein said pretreatment of the lignocellulosic biomass comprises applying a steam pressure selected within the range of from 8.0 to 15.0 bar.

8. Process according to claim 1, wherein the lignocellulosic biomass pretreatment is carried out for a time selected within the range of from 1 minute to 20 minutes.

* * * * *